United States Patent
Underwood

(10) Patent No.: US 12,005,096 B2
(45) Date of Patent: Jun. 11, 2024

(54) APOAEQUORIN AND VITAMIN D-CONTAINING COMPOSITIONS AND METHODS OF USING SAME

(71) Applicant: QUINCY BIOSCIENCE, LLC, Madison, WI (US)

(72) Inventor: Mark Y. Underwood, Madison, WI (US)

(73) Assignee: Quincy Bioscience, LLC, Madison, WI (US)

( * ) Notice: Subject to any disclaimer, the term of this patent is extended or adjusted under 35 U.S.C. 154(b) by 308 days.

(21) Appl. No.: 17/119,075

(22) Filed: Dec. 11, 2020

(65) Prior Publication Data

US 2021/0169981 A1 Jun. 10, 2021

Related U.S. Application Data

(63) Continuation of application No. 16/336,016, filed as application No. PCT/US2017/053279 on Sep. 25, 2017, now abandoned.

(60) Provisional application No. 62/398,669, filed on Sep. 23, 2016.

(51) Int. Cl.
| | |
|---|---|
| A61K 38/17 | (2006.01) |
| A23L 33/155 | (2016.01) |
| A23L 33/17 | (2016.01) |
| A61K 9/48 | (2006.01) |
| A61K 31/593 | (2006.01) |

(52) U.S. Cl.
CPC ........ A61K 38/1767 (2013.01); A23L 33/155 (2016.08); A23L 33/17 (2016.08); A61K 9/48 (2013.01); A61K 31/593 (2013.01)

(58) Field of Classification Search
CPC .... A61K 38/1767; A61K 9/48; A61K 31/593; A61K 2300/00; A23L 33/155; A23L 33/17; A61P 3/02; A61P 19/08; A61P 25/02; A61P 25/18; A61P 25/28; A61P 29/00; A61P 43/00; A23V 2200/00; A23V 2002/00; A23V 2250/543; A23V 2250/7106
See application file for complete search history.

(56) References Cited

U.S. PATENT DOCUMENTS

2014/0294874 A1 10/2014 Underwood

FOREIGN PATENT DOCUMENTS

| CN | 1752101 A | 3/2006 |
| KR | 10-2010-0136494 | 12/2010 |
| WO | 20090114597 A1 | 9/2009 |
| WO | 2016077437 | 5/2016 |

OTHER PUBLICATIONS

Balden et al., Endocrinology, May 2012, 153(5):2420-243 (Year: 2012).*
"Jellyfish Protein Shows Potential to Help with Memory", Internet Citation, Oct. 15, 2008 (Oct. 15, 2008), pp. 1-2, XP002528809, Retrieved from the Internet: URL: http://www.reuters.com/aarticle/pressRelease/idUS219580+15-Oct2008+PRN20081015 [retrieved on May 19, 2009] the whole document.
Julia A. Detert et al: "Pretreatment with Apoaequorin Protects Hippocampal CA1 Neurons from Oxygen-Glucose Deprivation", PLOS ONE, vol. 8, No. 11, Nov. 11, 2013 (Nov. 11, 2013), page e79002, XP055425497, DOI: 10,1371/journal.pone.0079002 the whole document.
Hideo Taniura et al: "Chronic vitamin D3 treatment protects against neurotoxicity by glutamate in association with upregulation of vitamin D receptor mRNA expression in cultured rat cortical neurons", Journal of Neuroscience Research., vol. 83, No. 7, Jan. 1, 2006 (Jan. 1, 2006), pp. 1179-1189, XP055426534, US ISSN: 0360-4012, DOI: 10.1002/jnr.20824 abstract, p. 1180, left-hand column.
PCT International Search Report, date of mailing Dec. 1, 2017.
Latimer et al., "Vitamin D Prevents Cognitive Decline and Enhances Hippocampal Synaptic Function in Aging Rats", PNAS, Sep. 29, 2014, E4359-E4366.
Kienreich et al., Vitamin D, arterial hypertension & cerebrovascular disease, Indian J Med Res 137, Apr. 2013, pp. 669-679.

* cited by examiner

Primary Examiner — Kimberly Ballard
Assistant Examiner — Stacey N MacFarlane
(74) Attorney, Agent, or Firm — Boyle Fredrickson S.C.

(57) ABSTRACT

Compositions containing apoaequorin and vitamin D and methods for their use in treating symptoms and disorders related to calcium imbalances and vitamin D deficiency associated with, for example, sleep quality, energy quality, mood quality, memory quality or pain are provided by the present invention.

12 Claims, 4 Drawing Sheets

Ischemia/No AQ/No VitD
CWS19 R1

No Ischemia/No AQ/No VitD
CWS19 R4

Ischemia/AQ/No VitD
CWS17 L4

No Ischemia/AQ/ No VitD
CWS19 L2

Ischemia/No AQ/ VitD
CWS10 R4

No Ischemia/No AQ/VitD
CWS07 L4

Ischemia/AQ/VitD
CWS07 R5

No Ischemia/AQ/VitD
CWS07 R4

APOAEQUORIN AND VITAMIN D-CONTAINING COMPOSITIONS AND METHODS OF USING SAME

CROSS-REFERENCE TO RELATED APPLICATIONS

This application claims the benefit of U.S. 371 National Phase Ser. No. 16/336,016, filed Mar. 22, 2019; which claims the benefit of PCT/US2017/053279, filed Sep. 25, 2017; which claims the benefit of U.S. Provisional application 62/398,669, filed Sep. 23, 2016, which are incorporated herein by reference in their entirety for all purposes.

STATEMENT REGARDING FEDERALLY SPONSORED RESEARCH OR DEVELOPMENT

Not Applicable.

FIELD OF THE INVENTION

This invention relates generally to compositions useful for the maintenance of calcium homeostasis. In particular, this invention is directed to apoaequorin and vitamin D-containing compositions useful in preventing and/or alleviating diseases or symptoms associated with calcium imbalance and vitamin D deficiency.

BACKGROUND OF THE INVENTION

Calcium is the fifth most abundant element in the human body and occurs mainly in the bone. More than 99% of the calcium in the body is stored in the skeleton, which constantly exchanges its supply with the remaining 1% dissolved in body fluids and soft tissue, such as the blood. The control of this exchange is largely dictated by the endocrine system which senses the concentration of ionized calcium in the plasma and directs calcium exchange to maintain this critical balance. Only a small fraction of the 1% of calcium in interstitial fluids and soft tissues is ionized and soluble. The remaining calcium in fluids and tissues is bound to proteins, particularly calcium-binding proteins (CaBPs). CaBPs are known to function in the maintenance of calcium homeostasis.

As the body requires specific concentrations of calcium ions to carry out requisite physiological processes, the maintenance of calcium homeostasis is of critical importance for bodily health. Proper ionic calcium concentrations in plasma and body fluids are understood by the medical community to be critical in bodily functions, including, but not limited to, neuronal excitability, muscle contraction, membrane permeability, cell division, hormone secretion and bone mineralization. A disruption in calcium homeostasis, i.e., a calcium imbalance, is associated with many diseases, syndromes and conditions, including, but not limited to, cancer, heart disease and neurodegenerative disease.

In the past, calcium channel antagonists, which block the flow of calcium between cell interiors and interstitial fluid, have been widely-prescribed as pharmaceutical agents useful in the prevention of calcium-related disorders including hypertension, angina, asthma, migraines and neural deterioration. For example, nimidopine has been found to improve clinical symptomatology and cognitive functions in dementia by alleviating a calcium imbalance which causes neural deterioration. However, many of these calcium channel antagonists have unwanted side effects including, but not limited to, malaise, fluid retention, heartburn, erratic heart rate, dizziness, upset stomach and, in rare cases, fainting, fever and excessive bleeding.

Despite these advances, there is still a need for new and alternative therapeutics which alleviate or prevent calcium imbalance. In particular, pharmaceutical or nutraceutical compositions which have reduced side effects as compared to prior agents are desired and, if discovered, would meet a long felt need in the medical and nutritional health communities.

SUMMARY OF THE INVENTION

The present invention provides compositions which are advantageous in the alleviation and/or prevention of symptoms or disorders associated with calcium imbalance and vitamin D deficiency. Such compositions include apoaequorin and vitamin D in combination with acceptable carriers for administration to a subject by a variety of routes.

Accordingly, the present invention is directed to compositions comprising effective amounts of apoaequorin and vitamin D in combination with an acceptable carrier. In certain embodiments, the present invention is directed to nutraceutical compositions including effective amounts of apoaequorin and vitamin D in combination with an acceptable carrier. In certain embodiments, nutraceutical compositions include, in addition to apoaequorin and vitamin D, at least one other component recognized as providing nutraceutical benefit such as, for example, an immune boosting agent, anti-inflammatory agent, anti-oxidant agent, anti-viral agent, or a mixture thereof. Apoaequorin and vitamin D compositions in certain embodiments are provided in a unit dosage form selected from a tablet, a capsule, a solution, a suspension, a syrup, a beverage, an oral or ophthalmic formulation or an injection.

In another aspect, the invention is directed to a method for treating a symptom or disorder associated with calcium imbalance and vitamin D deficiency, comprising administering to a subject in need of such treatment an effective amount of apoaequorin and vitamin D.

Methods according to the invention are useful in treating a wide variety of symptoms or disorders associated with calcium imbalance and vitamin D deficiency, including but not limited to sleep quality, energy quality, mood quality, pain, memory quality. In certain embodiments, the calcium imbalance and vitamin D deficiency is physiologically-related to neuronal excitability, muscle contraction, membrane permeability, cell division, hormone secretion, bone mineralization, or cell death following ischemia. In such methods, apoaequorin and vitamin D are preferably administered to the subject in the form of a nutraceutical composition.

In yet another embodiment, the invention encompasses the use of apoaequorin and vitamin D for the manufacture of a nutraceutical composition for treating a symptom or disorder associated with calcium imbalance and vitamin D deficiency in a subject administered the nutraceutical composition. Exemplary symptoms or disorders treated by such compositions include those associated with sleep, energy, mood, pain, or memory.

Accordingly, the present invention further contemplates apoaequorin and vitamin D for use in treating a symptom or disorder associated with calcium imbalance and vitamin D deficiency in a subject, including those symptoms or disorders associated with, e.g., sleep, energy, mood, pain, or memory in a subject.

The present invention provides various advantages over prior compositions and methods in that it provides for the general improvement of a subject's mental and physical health.

Other objects, features and advantages of the present invention will become apparent after review of the specification and claims.

DETAILED DESCRIPTION OF THE INVENTION

I. In General

Figure 1:
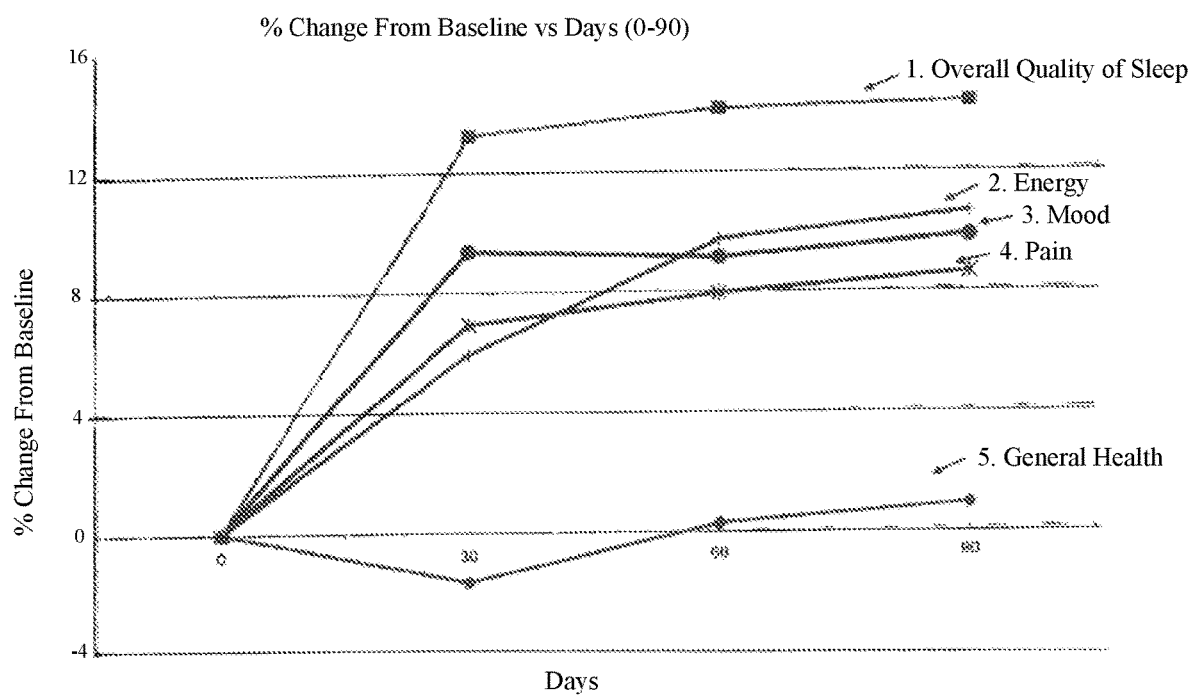
FIG. 1 provides a graph showing the percent change from baseline of scores from areas: overall quality of sleep, energy, mood, pain and general heath vs. days 0 through 90.

Before the present materials and methods are described, it is understood that this invention is not limited to the particular methodology, and materials described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes.

II. The Invention

Aequorin is a photo-protein originally isolated from luminescent jellyfish and other marine organisms. The aequorin complex comprises a 22,285-dalton apoaequorin protein, molecular oxygen and the luminophore coelenterazine. When three $Ca^2$ ions bind to this complex, coelenterazine is oxidized to coelentermide, with a concomitant release of carbon dioxide and blue light. Aequorin is not exported or secreted by cells, nor is it compartmentalized or sequestered within cells. Accordingly, aequorin measurements have been used to detect $Ca^2$ changes that occur over relatively long periods. In several experimental systems, aequorin's luminescence was detectable many hours to days after cell loading. It is further known that aequorin also does not disrupt cell functions or embryo development.

Because of its $Ca^2$-dependent luminescence, the aequorin complex has been extensively used as an intracellular $Ca^2$ indicator. *Aequorea victoria* aequorin has been specifically used to: (1) analyze the secretion response of single adrenal chromaffin cells to nicotinic cholinergic agonists; (2) clarify the role of $Ca^2$ release in heart muscle damage; (3) demonstrate the massive release of $Ca^2$ during fertilization; (4) study the regulation of the sarcoplasmic reticulum C2 pump expression in developing chick myoblasts; and (5) calibrate micropipets with injection volumes of as little as three picoliters.

Apoaequorin has an approximate molecular weight of 22 kDa. Apoaequorin can be used to regenerate aequorin by reducing the disulfide bond in apoaequorin. The calcium-loaded apoaequorin retains the same compact scaffold and overall folding patient as unreacted photoproteins containing a bound substrate.

Conventional purification of aequorin from the jellyfish *Aequorea victoria* requires laborious extraction procedures and sometimes yields preparations that are substantially heterogeneous or that are toxic to the organisms under study. Two tons of jellyfish typically yield approximately 125 mg of the purified photoprotein. In contrast, recombinant aequorin is preferably produced by purifying apoaequorin from genetically engineered *Escherichia coli*, followed by reconstitution of the aequorin complex in vitro with pure coelenterazine. Apoaequorin useful in the present invention has been described and is commercially-obtainable through purification schemes and/or syntheses known to those of skill in the art. S. Inouye, S. Zenno, Y. Sakaki, and F. Tsuji. *High level expression and Purification of apoaequorin.* (1991) Protein Expression and Purification 2,122-126.

Vitamin D is a group of fat-soluble secosteroids responsible for increasing intestinal absorption of calcium, iron, magnesium, phosphate, and zinc. Vitamin D is produced by the body in response to the skin being exposed to ultraviolet rays from sunlight. It is also found in naturally occurring foods such as fish, fish liver oils, egg yolks, and in fortified dairy and grain products. In dietary supplements, the two most common compound forms of vitamin D are vitamin D3 (cholecalciferol) and vitamin D2 (ergocalciferol).

Vitamin D is a fat soluble vitamin that is biologically inert and must undergo two hydroxylations in the body for activation. The first occurs in the liver and converts vitamin D to 25-hydroxyvitamin D [25(OH)D], also known as calcifediol. The second occurs primarily in the kidney and forms the physiologically active 1,25-dihydroxy vitamin D [1,25(OH)2D], also known as calcitriol. The active form of vitamin D, calcitriol, circulates as a hormone in the blood, regulating the concentration of calcium and phosphate in the bloodstream and promoting the healthy growth and remodeling of bone.

Vitamin D promotes calcium absorption and maintains adequate serum calcium and phosphate concentrations to enable normal mineralization of bone and to prevent hypocalcemic tetany. It is also used tor bone growth and bone remodeling by osteoblasts and osteoclasts. It has also been shown to play a role in modulation of cell growth, neuromuscular and immune function, and reduction of inflammation.

The present invention is directed to the administration of apoaequorin and vitamin D-containing compositions to a subject in order to correct or maintain the calcium balance and vitamin D levels in that subject. Vitamin D deficiency may contribute to calcium imbalances. The maintenance of ionic calcium concentrations in plasma and body fluids is understood to be critical to a wide variety of bodily functions, including, but not limited to neuronal excitability, muscle contraction, membrane permeability, cell division, hormone secretion, bone mineralization, or the prevention of cell death following ischemia. Disruption in calcium homeostasis, i.e., a calcium imbalance, is understood to cause and/or correlate with many diseases, syndromes and conditions. Such diseases, syndromes and conditions include those associated with sleep quality, energy quality, mood quality, and memory quality and pain perception. The study of CaBPs has led to their recognition as protective factors acting in the maintenance of proper ionic calcium levels.

The maintenance of vitamin D levels is understood to be critical to calcium absorption, modulation of cell growth, neuromuscular and immune function, and reduction of inflammation. Vitamin D deficiency is most associated with rickets, a disease in which the bone tissues does not properly mineralize, leading to soft bones and skeletal deformities. Guidelines from the Institute of Medicine provides that the recommended dietary allowance (RDA) of vitamin D is 600 international units (IU) for adults ages 1-70, and 800 IU for adults older than age 70 to optimize bone health.

In certain embodiments, the methods of the present invention comprise administering apoaequorin in combination with vitamin D for treating calcium imbalance, for delaying the progression of calcium imbalance, for preventing the onset of calcium imbalance, for preventing and/or treating the recurrence of calcium imbalance, and for treating vitamin D deficiency. In other embodiments, the invention provides methods which comprise administering apoaequorin and vitamin D in combination with one or more additional agents having known therapeutic or nutraceutical value. Particularly preferred applications of apoaequorin and vitamin D are in treating one or more symptoms and disorders related to quality of sleep, energy, mood, and memory and pain perception.

As used herein, the term "treating" includes preventative as well as disorder remittent treatment. As used herein, the terms "reducing", "alleviating", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cell in contact with apoaequorin and vitamin D. As used herein, administration can be accomplished in vitro, i.e., in a test tube, or in vivo, i.e., in cells or tissues of living organisms, for example, humans. In preferred embodiments, the present invention encompasses administering the compositions useful in the present invention to a patient or subject. A "patient" or "subject", used equivalently herein, refers to a mammal, preferably a human, that either: (1) has a calcium imbalance-related disorder and/or vitamin D deficiency remediable or treatable by administration of apoaequorin and vitamin D; or (2) is susceptible to a calcium imbalance-related disorder and or vitamin D deficiency that is preventable by administering apoaequorin and vitamin D.

As used herein, the terms "effective amount" and "therapeutically effective amount" refer to the quantity of active agents sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (1) the prevention of a calcium imbalance-related disorder and/or vitamin D deficiency; and (2) the reversal or stabilization of a calcium imbalance-related disorder and/or vitamin D deficiency. The optimum effective amounts can be readily determined by one of ordinary skill in the art using routine experimentation.

In certain compositions for oral administration to subjects, apoaequorin is formulated with at least one acceptable carrier at a dosage of approximately 10 to 50 mg/dose, a dose preferably in capsule form, with recommended dosage for a subject being approximately 20 mg/day. In certain preferred compositions for oral administration to subjects, vitamin D (in the form of D3 cholecalciferol) is formulated in combination with apoaequorin at a dosage of approximately 25-75 mcg/dose, with recommended dosage for a subject being approximately 50 mcg/day.

Compositions according to the present invention include liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, or hydrogels, or onto liposomes, microemulsions, micelles, lamellar or multilamellar vesicles, erythrocyte ghosts or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including parenteral, pulmonary, nasal and oral. In certain embodiments, the composition is administered parenterally, paracancerally, transmucosally, intramuscularly, intravenously, intradermally, subcutaneously, intraperitonealy, intraventricularly, intracranially or intratumorally.

Further, as used herein, "pharmaceutically acceptable carriers" are well known to those skilled in the art and include, but are not limited to, 0.0141M and preferably 0.05M phosphate buffer or 0.9% saline. Additionally, such pharmaceutically acceptable carriers may be aqueous or non-aqueous solutions, suspensions and emulsions. Examples of non-aqueous solvents are propylene glycol, polyethylene glycol, vegetable oils such as olive oil and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administrable according to the invention include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal, ophthalmic and oral.

Chemical entities modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the chemical entities solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-entity abducts less frequently or in lower doses than with the unmodified entity.

In yet another method according to tire invention, the composition can be delivered in a controlled release system. For example, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity to the therapeutic target, i.e., the brain, thus requiring only a fraction of the systemic dose.

The composition can comprise apoaequorin and vitamin D, or can further include a pharmaceutically acceptable carrier, and can be in solid or liquid form such as tablets, powders, capsules, pellets, solutions, suspensions, elixirs, syrups, beverages, emulsions, gels, creams, ophthalmic formulations, or suppositories, including rectal and urethral suppositories. Pharmaceutically acceptable carriers also include gums, starches, sugars, cellulosic materials, and mixtures thereof. The composition containing apoaequorin and vitamin D can be administered to a patient by, for example, subcutaneous implantation of a pellet. In a further embodiment, a pellet provides for controlled release of apoaequorin and/or vitamin D over a period of time. The composition can also be administered by intravenous, intraarterial, intramuscular injection of a liquid, oral administration of a liquid or solid, or by topical application. Administration can also be accomplished by use of a rectal suppository or a urethral suppository.

The compositions administrable by the invention can be prepared by known dissolving, mixing, granulating, or tablet-forming processes. For oral administration, apoaequorin or its physiologically-tolerated derivatives such as salts, esters, N-oxides, and the like and/or vitamin D or its physiologically-tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Compositions can be effected both as dry and as wet granules. For parenteral administration (subcutaneous, intravenous, intraarterial, or intramuscular injection), the chemical entity or its physiologically tolerated derivatives such as salts, esters, N-oxides, and the like are converted into a solution, suspension, or expulsion, if desired with the substances customary and suitable for this purpose, for example, solubilizers or other auxiliaries.

Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil or mineral oil. In general, water, saline, aqueous dextrose and related sugar solutions, and glycols such as propylene glycols or polyethylene glycol are preferred liquid carriers, particularly for injectable solutions.

The preparation of compositions which contain an active component is well understood in the art. Such compositions may be prepared as aerosols delivered to the nasopharynx or as injectables, either as a liquid solutions or suspensions; however, solid forms suitable for solution in, or suspension in, liquid prior to injection can also be prepared. The composition can also be emulsified. The active therapeutic ingredient is often mixed with excipients which are pharmaceutically acceptable and compatible with the active ingredient. Suitable excipients include, tor example, water, saline, dextrose, glycerol, ethanol, or the like or any combination thereof. In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric, or phosphoric acids, or such organic acids as acetic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like apoaequorin or its physiologically-tolerated derivates and/or vitamin D or its physiologically-tolerated derivates are prepared and applied as solutions, suspensions, or emulsions in a physiologically acceptable diluent with or without a pharmaceutical carrier.

In another method according to the invention, the active component can be delivered in a vesicle, in particular, a liposome (see Langer, Science 249:1527-1533 (1990); Treat et al., Liposomes in the Therapy of Infectious Disease and Cancer, Lopez-Berestein and Fidler (eds.), Liss, N.Y., pp. 353-365 (1989).

Salts of apoaequorin and/or vitamin D are preferably pharmaceutically acceptable salts. Other salts may, however, be useful in the preparation of the compositions according to the invention or of their pharmaceutically acceptable salts. Suitable pharmaceutically acceptable salts include acid addition salts which may, for example, be formed by mixing a solution of apoaequorin and/or vitamin D with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, taitaric acid, carbonic acid or phosphoric acid.

In addition, apoaequorin and vitamin D-containing compositions described herein may be provided in the form of nutraceutical compositions where apoaequorin and vitamin D prevent the onset of or reduce or stabilize various deleterious calcium imbalance-related disorders and vitamin D deficiency. The term "nutraceutical" or "nutraceutical composition", for the purpose of this specification, refers to a food item, or a part of a food item, that offers medical health benefits, including prevention and or treatment of disease. A nutraceutical composition according to the present invention may contain only apoaequorin and vitamin D as active ingredients, or alternatively, may further comprise, in admixture with dietary supplements including vitamins, co-enzymes, minerals, herbs, amino acids and the like which supplement the diet by increasing the total intake of that substance.

Therefore, the present invention provides methods of providing nutraceutical benefits to a patient comprising the step of administering to the patient a nutraceutical composition containing apoaequorin and vitamin D. Such compositions generally include a "nutraceutically-acceptable carrier" which, as referred to herein, is any carrier suitable for oral delivery including aforementioned pharmaceutically-acceptable carriers suitable for the oral route. In certain embodiments, nutraceutical compositions according to the invention comprise dietary supplements which, defined on a functional basis, include immune boosting agents, anti-inflammatory agents, anti-oxidant agents, anti-viral agents, or mixtures thereof.

Immune boosters and/or anti-viral agents are useful for accelerating wound-healing and improved immune function; and they include extracts from the coneflowers, or herbs of the genus *Echinacea*, extracts from herbs of the genus *Sambuca*, and Goldenseal extracts. Herbs of the genus *Astragalus* are also effective immune boosters in either their natural or processed forms. *Astragalus* stimulates development of stem cells in the marrow and lymph tissue active immune cells. Zinc and its bioactive salts, such as zinc gluconate and zinc acetate, also act as immune boosters in the treatment of die common cold.

Antioxidants include the natural, sulfur-containing amino acid allicin, which acts to increase the level of antioxidant enzymes in the blood. Herbs or herbal extracts, such as garlic, which contain allicin, are also effective antioxidants. The catechins, and the extracts of herbs such as green tea containing catechins, are also effective antioxidants. Extracts of the genus *Astragalus* also show antioxidant activity. The bioflavonoids, such as quercetin, hesperidin, rutin, and mixtures thereof, are also effective as antioxidants. The primary beneficial role of the bioflavonoids may be in protecting vitamin C from oxidation in the body. This makes more vitamin C, or ascorbic acid, available for use by the body.

Bioflavonoids such as quercetin are also effective anti-inflammatory agents, and may be used as such in the inventive compositions. Anti-inflammatory herbal supplements and anti-inflammatory compounds derived from plants or herbs may also be used as anti-inflammatory agents in the inventive composition. These include bromelain, a proteolytic enzyme found in pineapple; teas and extracts of stinging nettle; turmeric, extracts of turmeric, or curcumin, a yellow pigment isolated from turmeric.

Another supplement which may be used in the present invention is ginger, derived from herbs of the genus *Zingiber*. This has been found to possess cardiotonic activity due to compounds such as gingerol and the related compound shogaol as well as providing benefits in the treatment of dizziness, and vestibular disorders. Ginger is also effective in the treatment of nausea and other stomach disorders.

Supplements which assist in rebuilding soft tissue structures, particularly in rebuilding cartilage, are useful in compositions for treating the pain of arthritis and other joint disorders. Glucosamine, glucosamine sulfate, chondroitin may be derived from a variety of sources such as Elk Velvet Antler. Marine lipid complexes, omega 3 fatty acid complexes, and fish oil are also known to be useful in treating pain associated with arthritis.

Supplements useful in treating migraine headaches include feverfew and *Gingko biloba*. The main active ingredient in feverfew is the sesquiterpene lactone parthenolide, which inhibits the secretions of prostaglandins which in turn cause pain through vasospastic activity in the blood vessels. Feverfew also exhibits anti-inflammatory properties. Fish oil, owing to its platelet-stabilizing and antivasospastic actions, may also be useful in treating migraine headaches. The herb *Gingko biloba* also assists n treatment of migraines by stabilizing arteries and improving blood circulation.

Although some of the supplements listed above have been described as to their pharmacological effects, other supplements may also be utilized in the present invention and their effects are well documented in the scientific literature.

The invention will be more fully understood upon consideration of the following non-limiting Examples describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

EXAMPLES

Example 1

Administration of Apoaequorin Over a Ninety (90) Day Time Course Results in Improved Quality of Life for Test Subjects The present analysis, an open-label study, of 32 patients over a 90 day period shows an increase in overall quality of sleep, energy, mood, pain, general health. Changes in performance were measured via a standardized battery of questions. These included assessments of qualitative cognitive test, a sleep index, a headache index and a Quality of Life questionnaire. The study shows improved performance. No participants discontinued the study due to an adverse event.

The results illustrated in FIG. 1 show the percent change from baseline of scores from the areas mentioned; we have excluded the memory scores for another graph. The analysis here is shown as marked on the graph as 1, 2, 3, 4 and 5 vs. days 0 through 90. The graph shows an increase in overall quality of sleep, energy, mood, pain and general health. The baseline was known from a pre-study phase.

Example 2

Figure 2:
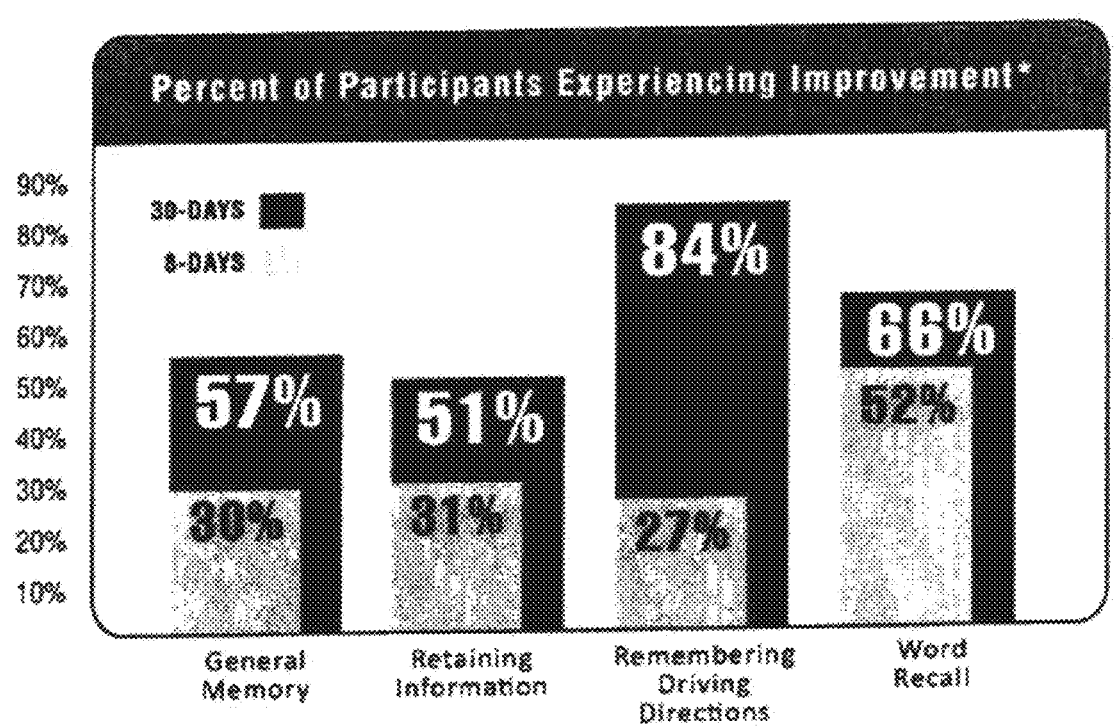
FIG. 2 depicts a graph showing data in which apoaequorin (10 mg) was taken daily by 56 participants. The participants were evaluated from eight days to 30 days. The memory study showed a statistically significant improvement in memory after 30 days (hp<0.05). 57% of participants had improvement in general memory, 51% in retaining information, 84% in remembering driving directions and 66% in word recall. N=56; 66% female, 34% male, mean age=56 years; range 20-78 years.

Administration of Apoaequorin Over a Thirty (30) Day Time Course Results in Improved Quality of Life for Test Subjects The present study was an open-label study for 56 participants over a 30 day period. Changes in performance were measured via a memory screening tool. As illustrated in FIG. 2, the study showed improved memory performance as early as eight days but with statistically greater improvement at day 30. No participants discontinued the study due to an adverse event.

Example 3

Figure 3:
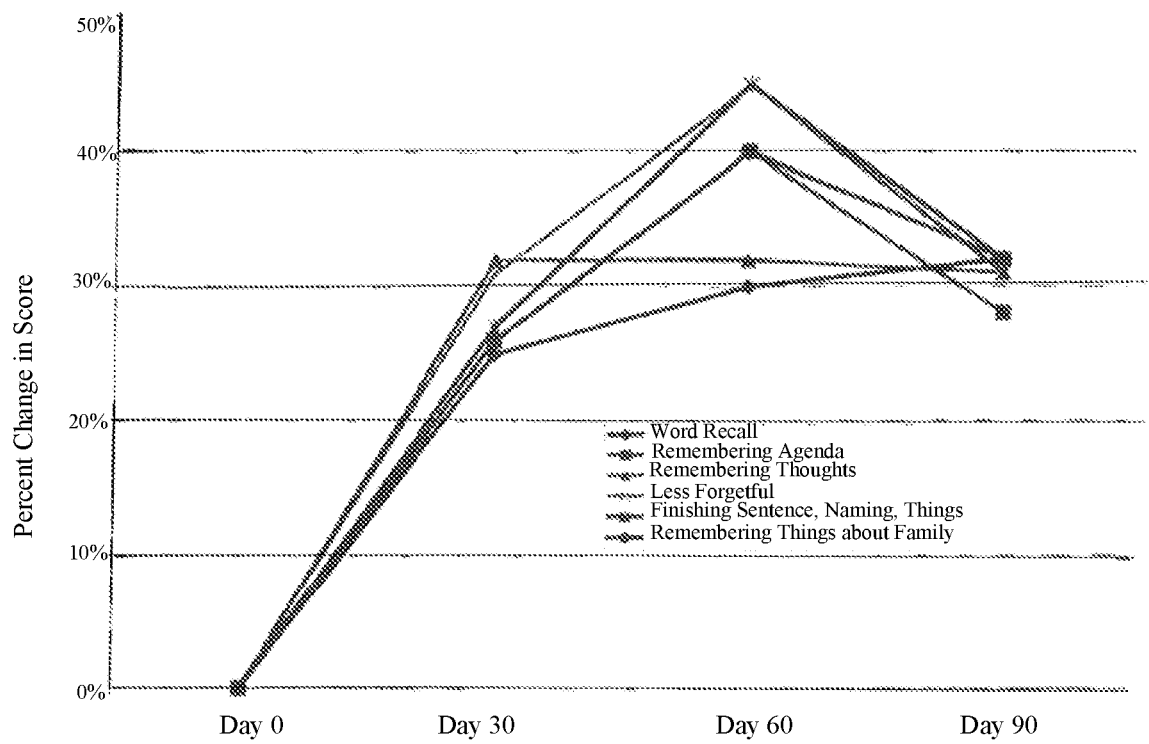
FIG. 3 provides a graph showing the percent change, from baseline, of scores from standardized cognitive battery questionnaire vs. day 0 through 90.

Administration of Apoaequorin Over a Ninety (90) Day Time Course Results in Improved Cognition for Test Subjects The present analysis, for an open-label study of 32 patients shows an increase in cognitive ability. Changes in performance were measured via a standardized cognitive battery. The study showed improved cognition as early as eight days but with statistically greater improvement at day 30, as well as 60-90. No participants discontinued the study due to an adverse event. The results shown in FIG. 3 demonstrate the significant percent increase from baseline of scores in cognitive ability. Note: Greater than 51% of participants had an increase in cognitive ability.

Example 4

Administration of Apoaequorin and Vitamin D-Containing Composition

An apoaequorin and vitamin D-containing composition is administered to a patient in capsule form containing an admixture of apoaequorin and vitamin D3. The composition contains 50 mcg of vitamin D3 (in the form of D3 cholecalciferol) and 20 mg of apoaequorin. The nutraceutical composition is carried in a nutraceutically-acceptable vegetable capsule (vegetable cellulose, water). The composition further contains microcrystalline cellulose, sugar, and small amounts of: acacia (gum Arabic), casein peptones, corn starch, lactose, magnesium stearate (vegetable source), medium chain triglycerides (vegetable oil), salt, soy peptones, DL-α-tocopherol, tricalcium phosphate, and water. One capsule taken daily provides a recommended dosage. Such dosage contains approximately 250% of the recommended daily allowance of vitamin D. Vitamin D suitable for use in the invention is available from BASF and sold as "Dry Vitamin D3 100 GFP/HP". The single dose may alternatively be formulated to contain other amounts of apoaequorin, including single dosages containing 10 mg or 40 mg of apoaequorin.

Example 5

Figure 4:
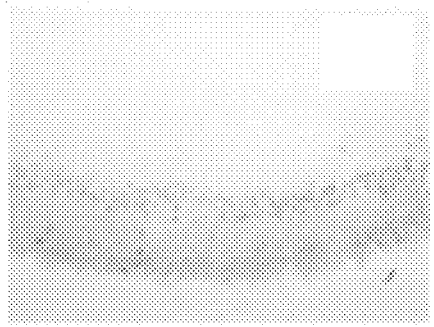
FIG. 4 depicts neuroprotection by AQ (apoaequorin) and Vitamin D in rat hippocampal brain slices.
Figure 4:
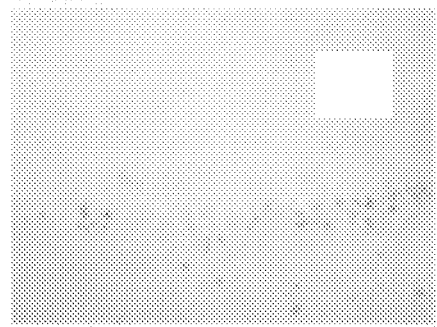
Figure 4:
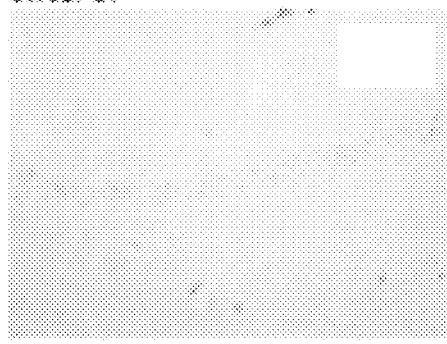
Figure 4:
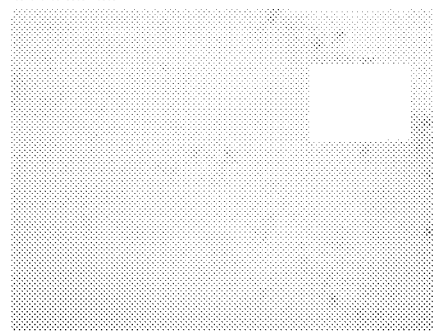
Figure 4:
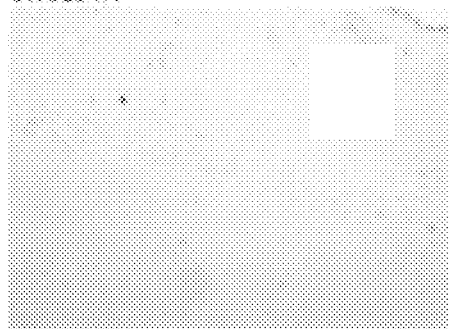
Figure 4:
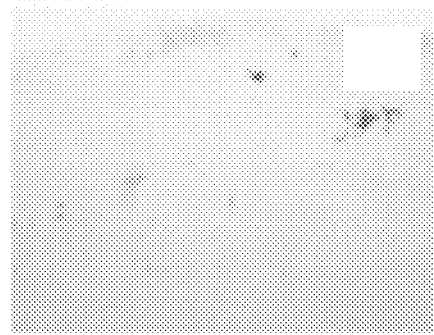
Figure 4:
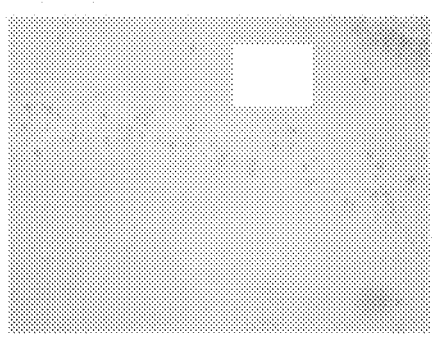
Figure 4:
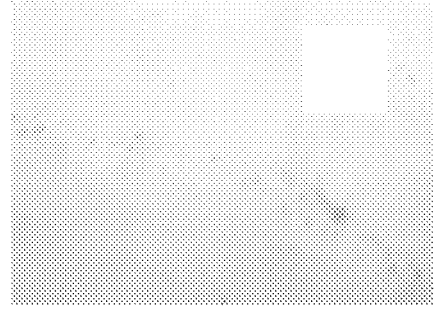

Evaluation of Neuroprotection by AQ (Apoaequorin) and Vitamin D in Rat Hippocampal Brain Slices Preliminary results from a subset of experimental data indicate significant cell death following 5-min of oxygen glucose deprivation (OGD FIG. 4; upper left image) and minimal cell death in slices that were not subjected to 5-min OGD (FIG. 4; upper right image). Direct hippocampal injection of AQ results in few er dead and dying cells (i.e., blue stained cells). Rats fed a diet supplemented with vitamin D (0.0125 mg/kg) for ~10 days also appear to have fewer dead or dying cells. The combination of AQ and vitamin D may further reduce the amount of cell death (FIG. 4; lower left image). Control slices (those not subjected to OGD) do not appear to vary appreciably as a function of treatment condition.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition for treating a symptom or disorder related to cell death following ischemia comprising:
    (a) a therapeutically effective amount of apoaequorin;
    (b) a therapeutically effective amount of vitamin D; and
    (c) an acceptable carrier
    wherein the therapeutically effective amount of apoaequorin is about 10 mg to 50 mg and the therapeutically effective amount of vitamin D is about 25 mcg to about 75 mcg.

2. The composition according to claim 1, wherein the composition is in the form of a unit dosage containing said effective amounts of the apoaequorin and vitamin D.

3. The composition according to claim 2, wherein: (a) the effective amount of apoaequorin in the unit dosage is about 20 mg; and (b) the effective amount of vitamin D in the unit dosage is about 50 mcg.

4. The composition according to claim 1, wherein the vitamin D is in the form of D3 cholecalciferol.

5. The composition according to claim 1, wherein the unit dosage is a capsule.

6. The composition according to claim 1, wherein the composition is a nutraceutical composition.

7. A method of administering a composition comprising administering to a subject an effective amount of the composition of claim 1.

8. The method according to claim 7, wherein administration of the composition to said subject improves sleep quality in the subject.

9. The method according to claim 7, wherein administration of the composition to said subject improves energy quality in the subject.

10. The method according to claim 7, wherein administration of the composition to said subject improves mood quality in the subject.

11. The method according to claim 7, wherein administration of the composition to said subject alleviates pain in the subject.

12. The method according to claim 7, administration of the composition to said subject improves memory quality in the subject.

* * * * *